US009615988B2

(12) United States Patent
Nakamura et al.

(10) Patent No.: US 9,615,988 B2
(45) Date of Patent: Apr. 11, 2017

(54) ARM SUPPORT APPARATUS

(71) Applicants: DENSO CORPORATION, Kariya, Aichi-pref. (JP); SHINSHU UNIVERSITY, Matsumoto, Nagano (JP); TOKYO WOMEN'S MEDICAL UNIVERSITY, Tokyo (JP)

(72) Inventors: Satoru Nakamura, Kariya (JP); Minoru Takahashi, Tokoname (JP); Hideki Okuda, Nagoya (JP); Kazuhiro Hongo, Matsumoto (JP); Tetsuya Goto, Matsumoto (JP); Yosuke Hara, Matsumoto (JP); Jun Okamoto, Tokyo (JP)

(73) Assignees: DENSO CORPORATION, Kariya (JP); SHINSHU UNIVERSITY, Nagano (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 14/483,337

(22) Filed: Sep. 11, 2014

(65) Prior Publication Data

US 2015/0202017 A1 Jul. 23, 2015

(30) Foreign Application Priority Data

Jan. 23, 2014 (JP) ................................. 2014-010383

(51) Int. Cl.
*B68G 5/00* (2006.01)
*A61G 15/10* (2006.01)
(Continued)

(52) U.S. Cl.
CPC .............. *A61G 15/10* (2013.01); *A61B 90/60* (2016.02); *A61G 13/10* (2013.01);
(Continued)

(58) Field of Classification Search
CPC ......... A47C 7/503; A47C 9/027; A47C 9/005; A61G 13/1235; A61G 2203/10
See application file for complete search history.

(56) References Cited

U.S. PATENT DOCUMENTS

| | | | | |
|---|---|---|---|---|
| 4,913,393 A | * | 4/1990 | Wood | ......................... 248/230.2 |
| 5,281,001 A | * | 1/1994 | Bergsten et al. | ........ 297/411.24 |

(Continued)

FOREIGN PATENT DOCUMENTS

| | | |
|---|---|---|
| JP | H10-272163 A | 10/1998 |
| JP | 2009-291363 A | 12/2009 |

OTHER PUBLICATIONS

Denso has developed an arm supporter that promises high operability in assisting neurosurgical operation, an article dated Sep. 12, 2013, Nikkan Kogyo Shinbun, Ltd (with partial English translation).

(Continued)

*Primary Examiner* — Amy Sterling
(74) *Attorney, Agent, or Firm* — Posz Law Group, PLC

(57) ABSTRACT

In arm support apparatus, a longitudinal mount has opposing first and second ends. An elbow locator is provided on the first end of the mount. The elbow locator locates an operator's elbow when the operator's forearm is mounted on the mount. A rotary joint of a multijoint arm has a rotary axis having a vertical component. The mount is rotatably joined to the rotary joint. While the forearm is mounted on the mount so that the elbow of the operator's arm is located by the elbow locator, the rotary axis is located with a distance with respect to the elbow to enable both the first and second ends of the mount to swing about the rotary axis. The distance is set to be equal to or longer than 50 mm.

9 Claims, 5 Drawing Sheets

(51) Int. Cl.
*A61G 13/10* (2006.01)
*A61B 90/60* (2016.01)
*A61G 13/12* (2006.01)

(52) U.S. Cl.
CPC ...... *A61G 13/1235* (2013.01); *A61G 2203/10* (2013.01); *A61G 2203/32* (2013.01)

(56) References Cited

U.S. PATENT DOCUMENTS

| | | | |
|---|---|---|---|
| 5,571,274 A * | 11/1996 | Holstensson | 297/411.38 |
| 5,927,815 A * | 7/1999 | Nakamura et al. | 297/411.38 |
| 6,773,071 B1 * | 8/2004 | Stasney et al. | 297/411.27 |
| 8,113,590 B2 * | 2/2012 | Stuijt | A61G 5/12 |
| | | | 297/411.35 |
| 8,480,168 B2 * | 7/2013 | Turner et al. | 297/195.11 |
| 2007/0215371 A1 * | 9/2007 | Wright | 173/185 |

OTHER PUBLICATIONS

Denso has developed an arm supporter that promises high operability in assisting neurosurgical operation, Mechanical Design (vol. 57), Nov. 2013, Nikkan Kogyo Shinbun, Ltd., p. 95 (with partial English translation).

\* cited by examiner

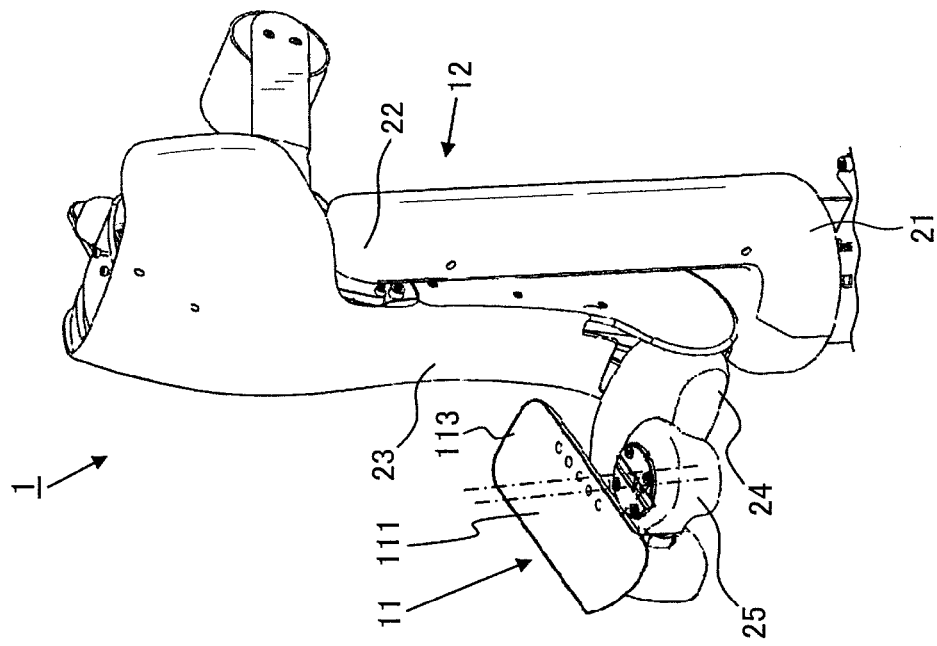
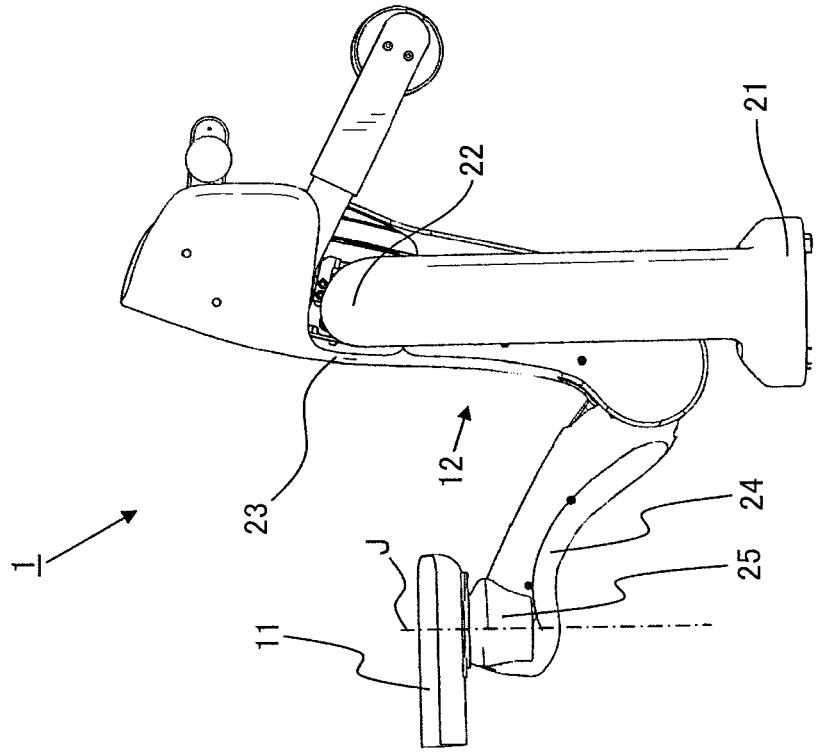

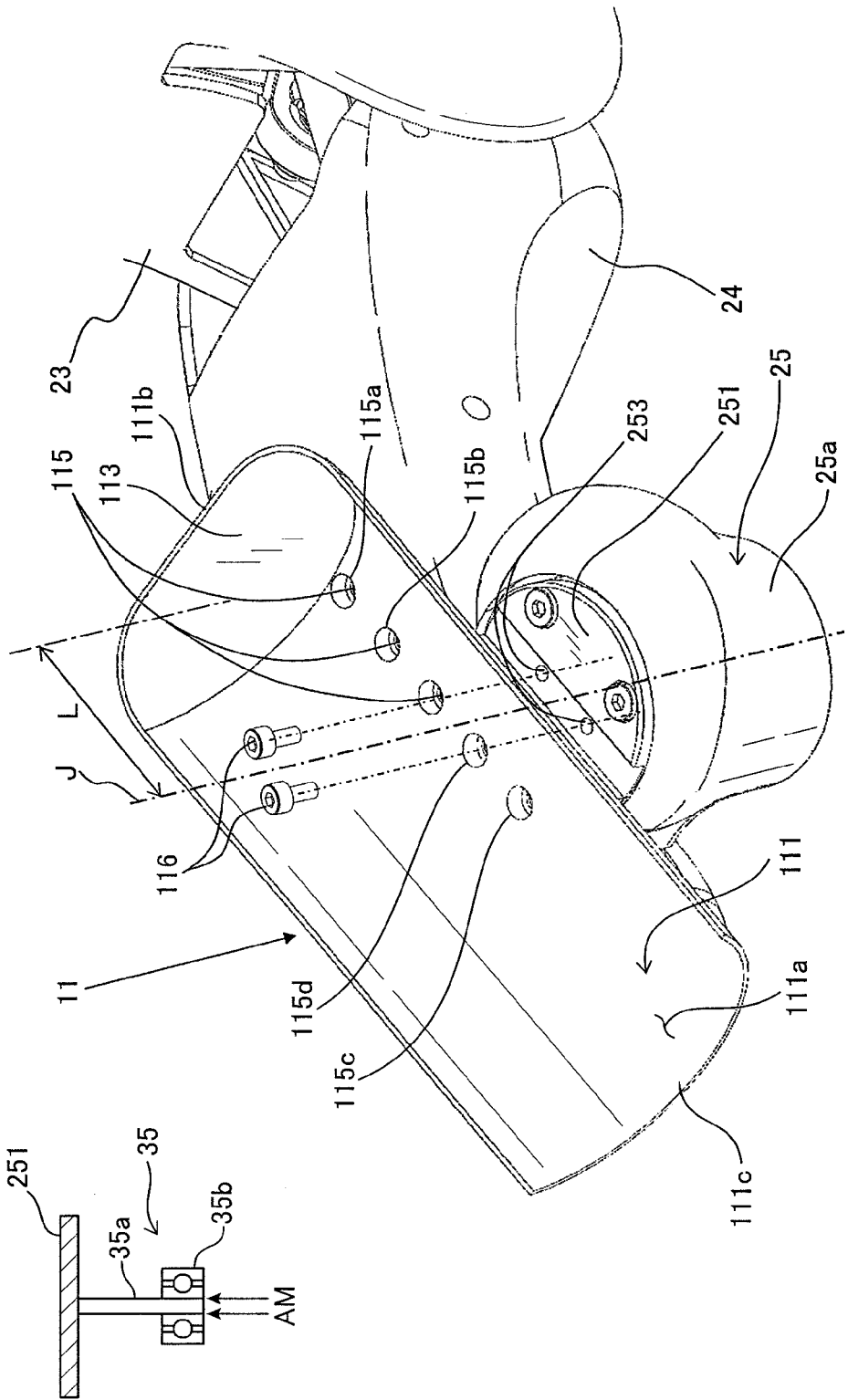

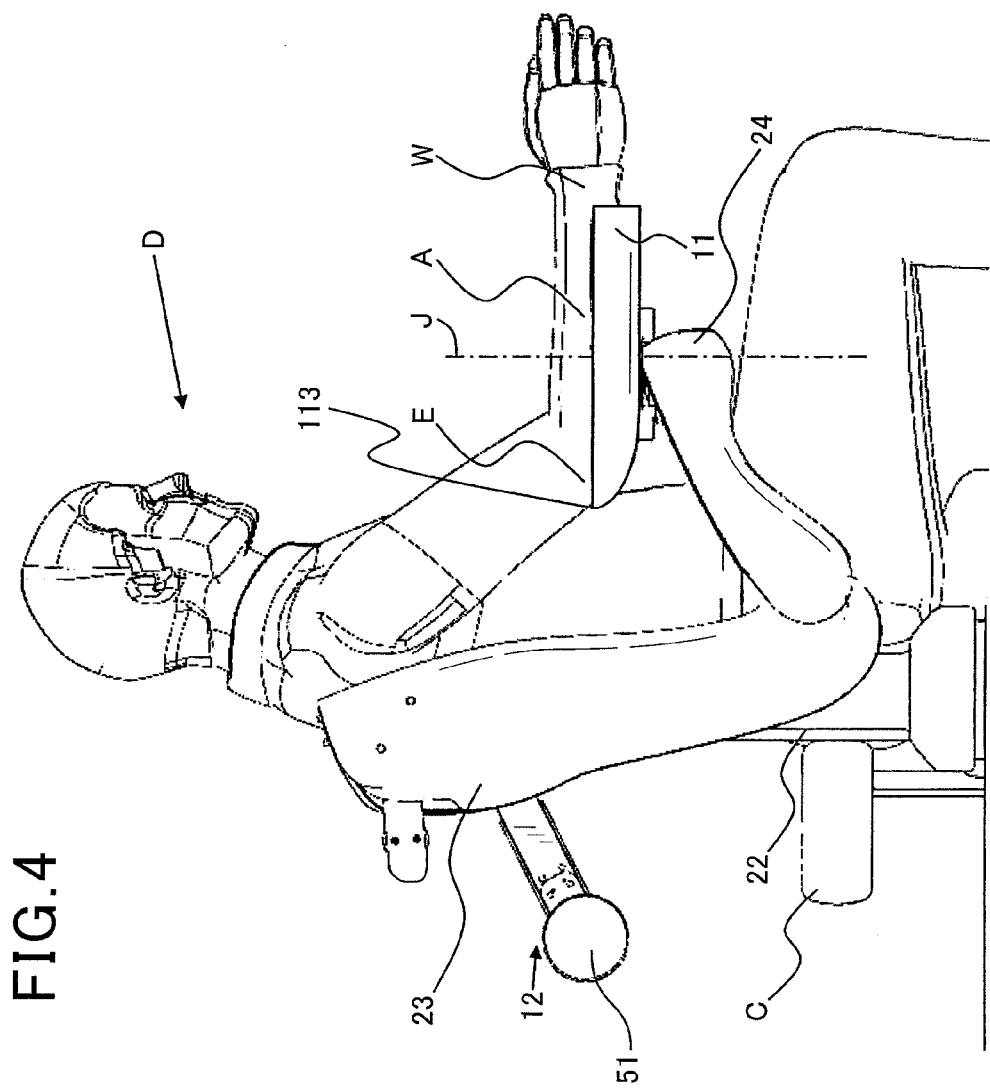

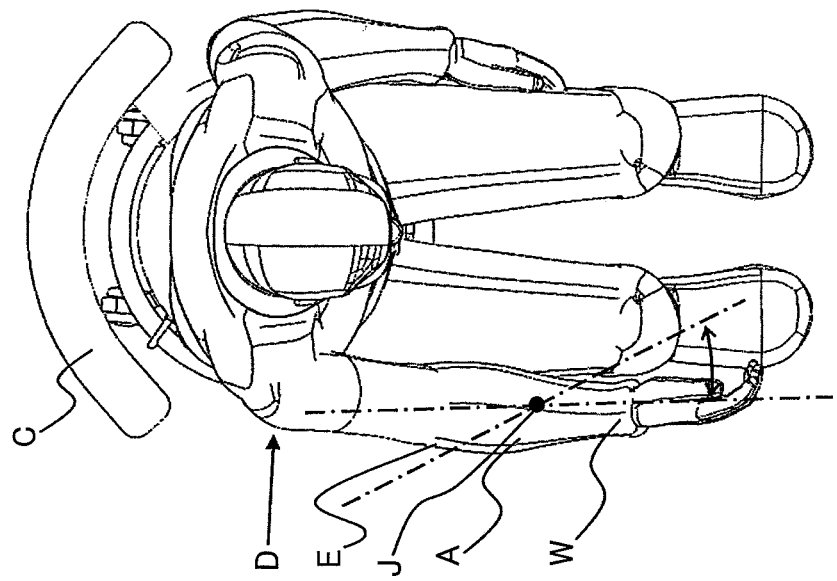
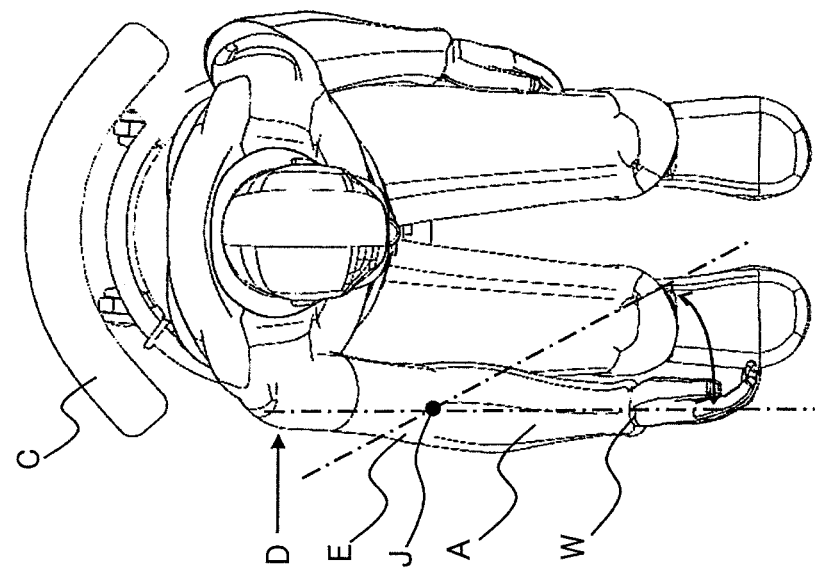

ARM SUPPORT APPARATUS

CROSS REFERENCE TO RELATED APPLICATIONS

This application is based on and claims the benefit of priority from Japanese Patent Application 2014-010383 filed on Jan. 23, 2014, the disclosure of which is incorporated in its entirety herein by reference.

TECHNICAL FIELD

The present disclosure relates to arm support apparatuses that support an arm of an operator and follow motion of the supported arm.

BACKGROUND

For precise and/or long manual operations, such as neurosurgical operations, there are known arm support apparatuses for supporting an arm an operator, such as a doctor that performs surgical operations. An example of these arm support apparatuses is disclosed in Japanese Patent Application Publication No. H10-272163, referred to as a first patent publication. An arm support apparatus disclosed in the first patent publication is equipped with a movable multijoint arm having a mount portion at an end thereof. The forearm of an operator's arm is fixedly mounted on the mount portion with a belt, which allows the mount portion to follow motion of the supported arm. The arm support apparatus is configured to lock the movable multijoint arm when a foot switch is operated by the operator, thus preventing motion of the mount portion.

The arm support apparatus disclosed in the first patent publication necessitates unfastening and fastening the belt each time the operator's arm is dismounted from the mount portion for mount of instrument, such as tweezers, on a table. This may result in the operator's usability of the arm support apparatus deteriorating.

In order to address such a problem, there is known an arm support apparatus, which is disclosed in Japanese Patent Application Publication No. 2009-291363, referred to as a second patent publication.

The arm support apparatus disclosed in the second patent publication is configured to urge the mount portion upward from the lower side of the mount portion to bring the mount portion into contact with the forearm of an operator's arm. This configuration permits the mount portion to follow movement of the operator's arm based on frictional resistance between the forearm of the operator's arm and the mount portion.

SUMMARY

In order to further improve the operator's operability using the arm support apparatus disclosed in each of the first and second patent publications, let us consider that an additional rotary joint is attached to the movable multijoint arm; the additional joint allows rotation of the mount portion for an operator's arm about a rotary axis of the additional rotary joint. In view of improvement of the operator's operability using the arm support apparatus, it is important where the additional joint is located relative to the mount portion. Thus, there are requirements for considering where the additional joint is located relative to the mount portion.

In view of the circumstances set forth above, one aspect of the present disclosure seeks to provide arm support apparatuses, each of which is designed to address these requirements set forth above.

Specifically, an alternative aspect of the present disclosure aims to provide such arm support apparatuses, each of which is capable of locating such an additional joint at a suitable position relative to a mount portion of a movable multijoint arm.

According to an exemplary aspect of the present disclosure, there is provided an arm support apparatus for supporting an arm of an operator. The arm support apparatus includes an arm holder having a longitudinal mount on which a forearm of the operator's arm is mountable. The longitudinal mount has a first end and a second end opposite to the first end in a longitudinal direction thereof. The arm support apparatus includes an elbow locator provided on the first end of the mount. The elbow locator locates an elbow of the operator's arm when the forearm is mounted on the mount. The arm support apparatus includes a multijoint supporting member having a plurality of joints and movably supporting the mount via motions of the joints. The arm support apparatus includes at least one weight provided on at least part of the multijoint supporting member, The at least one weight suppresses movement around at least one of the joints based on gravity while the forearm is mounted on the mount. The joints include a rotary joint having a rotary axis. The rotary axis has a vertical component and penetrates through the mount. The mount is rotatably joined to the rotary joint. While the forearm is mounted on the mount so that the elbow of the operator's arm is located by the elbow locator, the rotary axis is located with a distance with respect to the elbow to enable both the first and second ends of the mount to swing about the rotary axis. The distance is set to be equal to or longer than 50 mm.

This configuration prevents or limits, while the forearm is mounted on the mount, the forearm mounted on the mount from swinging about the elbow located by the elbow locator. In other words, the length of the distance is determined to prevent or limit, while the forearm is mounted on the mount, the forearm mounted on the mount from swinging about the elbow located by the elbow locator. Thus, the value 50 mm of the distance can be changed as long as the changed value of the distance prevents or limits, while the forearm is mounted on the mount, the forearm mounted on the mount from swinging about the elbow located by the elbow locator.

As a result, the configuration prevents or limits the operator's fingertips from largely swinging about the rotary axis even if the operator moves, i.e. swings, the elbow about the rotary axis, resulting in maintenance of operator's operability of the fingerprints using the arm support apparatus.

As a modification, in the exemplary aspect of the present disclosure, the feature that, while the forearm is mounted on the mount so that the elbow of the operator's arm is located by the elbow locator, the rotary axis is located with a distance with respect to the elbow to enable both the first and second ends of the mount to swing about the rotary axis; the distance being set to be equal to or longer than 50 mm, can be changed to the following feature:

while the forearm is mounted on the mount so that the elbow of the operator's arm is located by the elbow locator, the rotary axis is located with a distance with respect to the first end of the mount, the distance enabling both the first and second ends of the mount to swing about the rotary axis while preventing or limiting the mount from swinging about the elbow locator.

Various aspects of the present disclosure can include and/or exclude different features, and/or advantages where applicable. In addition, various aspects of the present disclosure can combine one or more feature of other embodiments where applicable. The descriptions of features, and/or advantages of particular embodiments should not be construed as limiting other embodiments or the claims.

BRIEF DESCRIPTION OF THE DRAWINGS

Other aspects of the present disclosure will become apparent from the following description of embodiments with reference to the accompanying drawings in which:

FIG. 1A is a left-side view of an arm support apparatus according to an exemplary embodiment of the present disclosure;

FIG. 1B is a perspective view of the arm support apparatus illustrated in FIG. 1A;

FIG. 3A is an enlarged perspective view of an arm holder and a holder supporter of the arm support apparatus illustrated in FIGS. 1A and 1B;

FIG. 3B is a longitudinal cross sectional view of a rotating plate and a joint of the holder supporter;

FIG. 4 is a right-side view of the arm support apparatus while a doctor sits on a chair by the arm support apparatus and mounts the forearm on the arm holder according to the exemplary embodiment;

FIG. 5A is a plan view of the doctor, which illustrates the relative positional relationship between a rotary axis about which the rotating plate rotates and the elbow of the doctor according to a comparative example for the exemplary embodiment; and FIG. 5B is a plan view of the doctor, which illustrates the relative positional relationship between the rotary axis about which the rotating plate rotates and the elbow of the doctor according to the exemplary embodiment.

DETAILED DESCRIPTION OF EMBODIMENT

Figure 2:
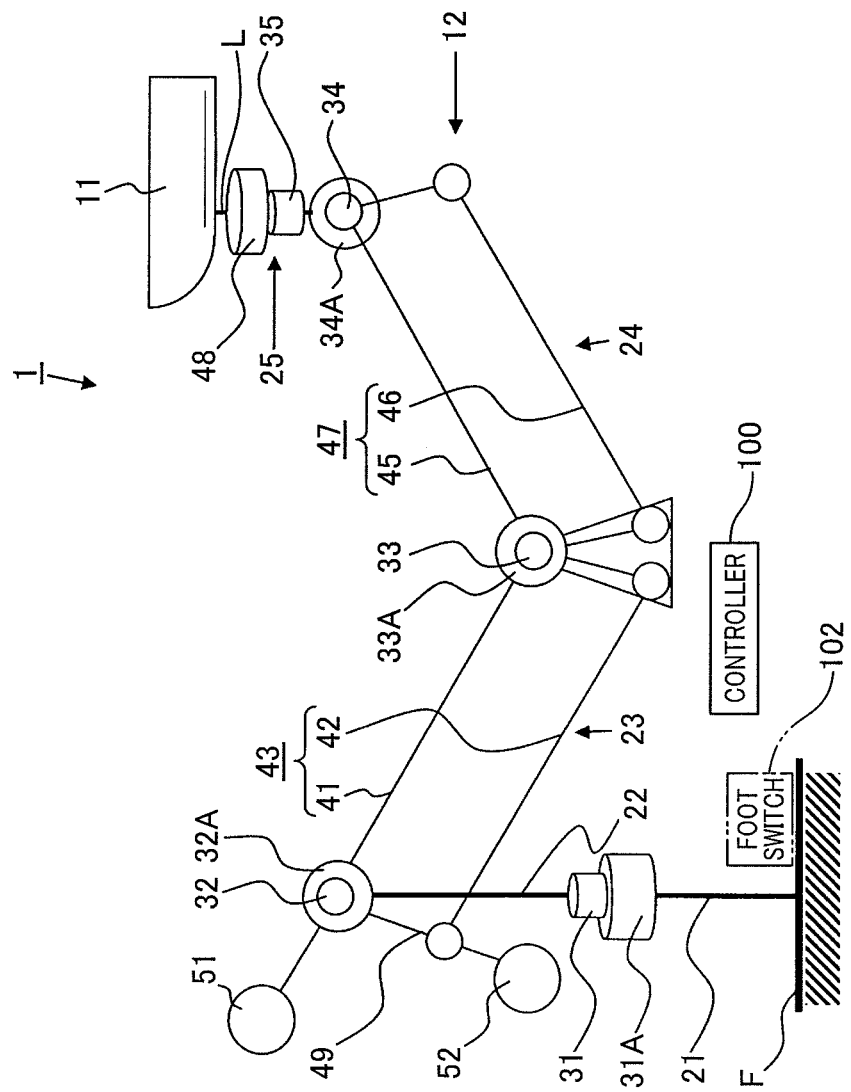
FIG. 2 is a schematic view of the arm support apparatus according to the exemplary embodiment of the present disclosure.

An exemplary embodiment of the present disclosure will be described hereinafter with reference to the accompanying drawings. In the drawings, identical reference characters are utilized to identify identical corresponding components.

FIGS. 1A and 1B schematically illustrate the outward appearance of an arm support apparatus 1 according to the exemplary embodiment of the present disclosure.

Referring to FIGS. 1A and 1B, the arm support apparatus 1 is operative to support a part of an arm, i.e. the forearm A of the dominant arm, i.e. right or left arm, of a doctor D (see FIG. 4). Specifically, the arm support apparatus 1 includes a multijoint arm serving as a multijoint supporting member 12 and an arm holder 11, which is an example of mount portions movably supported by the multijoint arm 12; the forearm A of the dominant arm of the doctor D is to be fixedly mounted on the arm holder 11. The arm support apparatus 1 also includes a controller 100 (see FIG. 2) for controlling motion of each of the multijoint arm 12 and the arm holder 11.

The multijoint arm 12 is comprised of a base 21, a shoulder 22, a first arm portion 23, a second arm portion 24, and a holder supporter 25. The multijoint arm 12 also has, for example, five rotational joints 31, 32, 33, 34, and 35 that provide five degrees of freedom.

The base 21 has a substantially column shape, and is located on a floor F of an operating room. The base 21 is configured to support the remaining parts of the multijoint arm 12. In this embodiment, the base 21 is fixed to the floor F, but can be movably located on the floor F. When the base 21 is movably located on the floor F, the base 21 has a stopper (not shown) that allows an operator to fixedly locate the base 21 at a desired position of the floor F.

The shoulder 22 extends perpendicularly from the base 21, and is rotatable about an axis on the base 21 perpendicular to the floor F. The first arm portion 23 has a first end and a second end opposite to the first end. The first end of the first arm portion 23 is pivotally joined to a top end of the shoulder 22 about a horizontal axis at the top end of the shoulder 22. The second arm portion 24 has a first end and a second end opposite to the first end. The first end of the second arm portion 24 is pivotally joined to the second end of the first arm portion 23 about a horizontal axis at the second end of the first arm portion 23. The holder supporter 25 is pivotally joined to the second end of the second arm portion 24 about a horizontal axis at the second end of the second arm portion 24. The holder supporter 25 pivotally supports the arm holder 11 about a rotary axis J, which has a vertical component and is, for example, substantially perpendicular to the horizontal axis at the second end of the second arm portion 24.

FIG. 2 schematically illustrates the arm support apparatus 1 according to the exemplary embodiment of the present disclosure. Specifically, FIG. 2 schematically illustrates the arm support apparatus 1 mainly using links corresponding to the respective base 21, shoulder 22, first arm portion 23, second arm portion 24, and holder supporter 25, and the joints 31 to 35.

The base 21 serves as a base link 21 mounted on the floor F. A top of the base link 21 is joined to the joint 31, and the joint 31 has an axis perpendicular to, for example, the floor F. The shoulder 22 serves as a shoulder link 22 has a longitudinal shape, a first end, and a second end opposite to the first end in the longitudinal direction thereof. The first end of the shoulder link 22 is joined to the joint 31 to be rotatable about the axis of the joint 31 based on motion of the joint 31. The joint 32 has a horizontal axis and is attached to the second end of the shoulder link 22.

The first arm portion 23 includes a parallel link mechanism 43 comprised of a set of first and second links 41 and 42. The first and second links 41 and 42 are configured to move while keeping the first and second links 41 and 42 in parallel to each other with a constant interval therebetween.

Specifically, the first link 41 has a first end and a second end opposite to the first end, and the second link 42 has a first end and a second end opposite to the first end. The first end of the first link 41 is joined to the first end of the second link 42 via a link 49, and the second end of the first link 41 is joined to the second end of the second link 42.

The first end of the first link 41 is joined to the joint 32 to be swingable about the horizontal axis of the joint 32 based on motion of the joint 32.

The second arm portion 24 includes a parallel link mechanism 47 comprised of a set of first and second links 45 and 46. The first and second links 45 and 46 are configured to move while keeping the first and second links 45 and 45 in parallel to each other with a constant interval therebetween.

The first end of the first link 45 is joined to the first end of the second link 46, and the second end of the first link 45 is joined to the second end of the second link 46.

The joint 33 has a horizontal axis. The second end of the first link 41 of the first arm portion 23 and the first end of the first link 45 of the second arm portion 24 are joined to each other via the joint 33 to be swingable about the horizontal axis of the joint 33 based on motion of the joint 33.

The joint 34 has a horizontal axis, and is located on the second end of the first link 45 of the second arm 24. A link L has a first end and a second end opposite to the first end. The first end of the link L is joined to the joint 34 to be pivotable about the horizontal axis of the joint 34 based on motion of the joint 34. The link L includes the joint 35 having a rotary axis. The arm holder 11 is attached to the second end of the link L to be rotatable about the rotary axis of the joint 35 based on motion of the joint 35. A force sensor 48 is attached to the joint 35 and operative to measure force applied to the arm holder 11 from the forearm A. The force sensor 48 is communicably connected to the controller 100, and operative to send force measured thereby to the controller 100.

The first link 41 has an extension extending from the first end thereof through the joint 32 to be far from the joint 32 by a preset length. To the extending end of the extension of the first link 41, counterweights 51 are attached.

The counterweights 51 are operative to, when the forearm A of the doctor's dominant arm is fixedly mounted on the arm holder 11, apply counterbalance force to the arm holder 11 and the multijoint arm 3 to suppress gravitational movement from acting around the joint 32.

One end of the link 49 joined to the first end of the link 42 of the first link mechanism 43 extends through the first end of the link 42 to be far from the first end of the link 42. To the extending end of the link 49, counterweights 52 are attached.

The counterweights 52 are operative to apply counterbalance force to the arm holder 11 and the multijoint arm 3 while the forearm A of the doctor's dominant arm is mounted on the arm holder 11 to suppress gravitational movement from acting around the joint 34. Specifically, the counterweights 51 and 52 are an example of weights.

To the respective joints 31, 32, 33, and 34 except for the joint 35, brakes, such as electromagnetic brakes, 31A, 32A, 33A, and 34A are attached.

Each of the brakes 31A to 34A is operative to limit motion of a corresponding one of the joints 31 to 34, i.e. limit pivot of a corresponding one of the shoulder 22, the first arm portion 23, the second arm portion 24, and the arm holder 11 about a corresponding one of the joints 31 to 34.

In the exemplary embodiment, each of the brakes 31A, 32A, 33A, and 34A is operative to lock a corresponding one of the joints 31, 32, 33, and 34, thus locking the shoulder 22, the first arm portion 23, the second arm portion 24, and the arm holder 11 from pivoting about a corresponding one of the joints 31, 32, 33, and 34.

The brakes 31A to 34A are controllably connected to the controller 100. The controller 100 is designed to operate in a lock mode for activating the brakes 31A to 34A to limit, i.e. lock, motion of the arm holder 11, and operate in a free mode for deactivating the brakes 31A to 34A to allow free movement of the arm holder 11.

Specifically, the lock mode is designed assuming that the forearm A of the dominant arm of the doctor D is mounted on the arm holder 11 for performing surgical operations. In the lock mode, the controller 100 activates the brakes 31A, 32A, 33A, and 34A to stop motion of the corresponding joints 31, 32, 33, and 34, thus preventing movement of the arm holder 11. In the lock mode, if the doctor D removes the forearm A from the arm holder 11, the position of the arm holder 11 is locked. In the lock mode, because no brakes are attached to the joint 35, the arm holder 11 is freely rotatable about the rotary axis J in the lock mode.

In contrast, the free mode is designed assuming that the doctor D intends to make the arm holder 11 follow movement of the forearm A. In the free mode, the controller 100 maintains deactivation of the brakes 31A, 32A, 33A, and 34A to allow free motion of the corresponding joints 31, 32, 33, and 34, thus allowing free motion of the arm holder 11.

Specifically, in the free mode, when the doctor D moves the forearm A, the arm holder 11 follows the movement of the forearm A. This is because the joints 31 to 34 can move freely and the forearm A is fixedly supported on the arm holder 11. In addition, force applied from the arm holder 11 to the forearm A is very weak force, and slide resistance of each of the brakes 31A to 34A is small. Thus, the doctor D can easily move the arm holder 11 to follow movement of the forearm A using weak force applied to the forearm A.

In the exemplary embodiment, a foot switch 102 as an example of manual switches can be located on the floor F as an element of the arm support apparatus 1. The foot switch 102 is communicably coupled to the controller 100, and capable of sending an instruction to the controller 100 each time the doctor D operates, i.e. depresses the foot switch 102 using a foot. When the instruction is sent to the controller 100, the controller 100 can be, for example, configured to switch the current operation mode, i.e. one of the lock mode and the free mode, to the other mode thereof. The controller 100 can be configured to switch the current operation mode thereof between the free mode and the lock mode based on value of the force measured by the force sensor; the force is applied to the arm holder 11 from the forearm A. For example, the doctor D applies given force to the arm holder 11 from the forearm A, it is possible to switch the current operation mode to one of the free mode and the lock mode.

Referring to FIG. 3A, the arm holder 11 includes a rectangular plate-like longitudinal mount 111 having a substantially U shape in its lateral cross section.

Specifically, the mount 111 has a concaved bottom wall and an opening top wall extending in a longitudinal direction thereof. The concaved bottom wall has an inner surface, i.e. a mount surface, 111a, on which the forearm A is mountable. The mount 111 has a first end 111b and a second end 111c longitudinally opposite to the first end 111b. The first end 111b is closer to the multijoint arm 12 than the second end 111c is.

Because the lengths of operators are usually included in the range from 250 to 300 mm inclusive, the longitudinal length of the mount is determined based on the range.

One end portion of the mount 111 including the first end 111b is elevated, so that the elevated end portion of the mount 111 serves as an elbow locator 113 as an example of various locators. Specifically, when the doctor D mounts the forearm A of the dominant arm on the mount surface 111a while the hand portion of the dominant arm projects from the second end 111c, the elbow E of the dominant arm abuts on the elbow locator 113. This locates the position of the elbow E of the dominant arm.

The concaved bottom wall of the mount 111 has a plurality of circular adjustment holes 115 formed at its longitudinal center portion therethrough. In the exemplary embodiment, five circular adjustment holes 115 are formed through the concaved bottom wall with, for example, regular intervals in the longitudinal direction of the concaved bottom wall.

The holder supporter 25 includes a substantially cylindrical inner-hollow housing 25a joined to the second end of the second arm portion 24 while the center axis of the housing 25a is parallel to the vertical direction of the floor F. The joint 35 is rotatably installed in the housing 25a such that the rotary axis J of the joint 35 is coaxial to the center axis of the housing 25a. The holder supporter 25 also includes a substantially circular rotating plate 251 rotatably mounted over a top of the housing 25a about the rotary axis J. For example, the joint 35 has a rotating shaft 35a corresponding to the rotary axis J, and a bearing 35b rotatably supporting one end of the rotating shaft (see FIG. 3B). The other end of the rotating shaft 35a is attached to the rotating plate 251. This permits the rotating plate 251 to rotate about the rotary axis J.

The rotating plate 251 has fromed on a center portion of its top surface with two bolt holes 253; the two bolt holes 253 has an interval therebetween matching with the intervals of the five adjustment holes 115. That is, the arm holder 11 is mounted on the top surface of the rotating plate 251 while selected adjacent two adjustment holes 115 are aligned with the respective two bolt holes 253. Two bolts 116 are inserted through the selected adjacent two adjustment holes 115 into the respective two bolt holes 253 from the opening top-wall side of the mount 111. This causes male (external) threads of the two bolts 116 to be respectively meshed with female (internal) threads of the respective two bolt holes 253 while the heads of the two bolts 116 are fitted in the respective adjustment holes 115. This therefore results in the mount 111 being fixedly mounted on the rotating plate 251, which allows the mount 111 to rotate based on rotation of the rotating plate 251, i.e. the joint 35.

Selection of adjacent two adjustment holes in the five adjustment holes 115, which are fixed to the bolt holes 253 via the bolts 116, permits adjustment of an interval, i.e. a minimum distance, L between the rotary axis J and an outwardly point end, i.e. an outwardly projecting end, of the bone of the elbow E of the dominant arm located on the elbow holder 113.

Strictly speaking, while the dominant arm is bent and the forearm A is mounted on the mount surface 111a of the mount 111, the point end of the elbow E appears, so that a minimum distance is defined as the interval L between the point end of the elbow E and a portion of the rotary axis J; the portion faces the point end of the elbow E and has the same height as that of the point end of the elbow E.

As illustrated in FIG. 3, when adjacent two adjustment holes 115a and 115b, which are closest to the first end 111b in the five adjustment holes 115, are selected to be fixed to the bolt holes 253 via the bolts 116, the interval L is set to be equal to or longer than 50 mm. Preferably, when the adjacent two adjustment holes 115a and 115b are selected to be fixed to the bolt holes 253 via the bolts 116, the interval L is set to be equal to or longer than 70 mm.

In contrast, when adjacent two adjustment holes 115c and 115d, which are farthest from the first end 111b in the five adjustment holes 115, are selected to be fixed to the bolt holes 253 via the bolts 116, the interval L is set to be equal to or shorter than 100 mm. Pitches between the center axes of adjacent adjustment holes 115 can be designed in consideration of the length of the forearm of a doctor D and/or the doctor's needs. Preferably, the pitches between the center axes of adjacent adjustment holes 115 are set to be within the range from 10 to 15 mm inclusive.

Rotational resistance of the rotating plate 251, i.e. sliding friction between the rotating shaft 35a and the bearing 35b, is adjusted to be variably set within a range from 0.01 to 0.1 Nm inclusive. For example, a rotational-resistance adjusting member AM, such as a plunger, a rubber member, or the like, is provided in abutment on, for example, the rotating shaft 35a to adjust the rotational resistance to be within the range from 0.01 to 0.1 Nm inclusive.

Technical effects achieved by the configuration of the arm support apparatus 1 will be described hereinafter.

Referring to FIG. 4, when a doctor D uses the arm support apparatus 1, the doctor D prepares a chair C and locates the chair C by the arm support apparatus 1. Then, the doctor D sits on the chair C, and puts the forearm A of the dominant arm, i.e. the right arm, on the arm holder 11 while sitting on the chair C.

When the doctor D applies given force to the arm holder 11 from the forearm A to switch the operation mode of the arm support apparatus 1 to the free mode, the doctor D makes the arm holder 11 easily follow motion of the forearm A. Specifically, the counterweights 51 and 52 apply counterbalance force to the arm holder 11 and the multijoint arm 3 while the forearm A of the doctor's dominant arm is mounted on the arm holder 11 to prevent gravitational movement from acting around each of the joints 32 and 34. In other words, movement based on the weight of the forearm A is balanced with movement based on the counterweights 51 and 52, so that the arm holder 11 is pressed to be in contact with the forearm A by the same force as the weight of the forearm A.

This configuration permits the arm holder 11 to smoothly follow movement of the forearm A based on frictional resistance between the forearm A and the arm holder 11 pressed to be in contact with the forearm A.

The balancing of movement prevents the arm holder 11 on which the forearm A is mounted from being unintendedly moved due to the weight of the forearm A. In addition, the balancing of movement suppresses redundant force from being applied to the forearm A from the arm holder 11.

The end portion of the mount 111 of the arm holder 11 including the first end 111b, which is closer to the multijoint arm 12 than the second end 111c is, is evaluated to serve as the elbow locator 113. Specifically, when the doctor D mounts the forearm A of the dominant arm on the mount surface 111a while, for example, the hand portion of the dominant arm projects from the second end 111c, the elbow E of the dominant arm abuts on the elbow locator 113. This locates the position of the elbow E of the dominant arm. This results in smooth movement of the arm holder 11 in the longitudinal direction of the forearm A. Note that, in view of improvement of operability using the dominant arm in, at least the finger portion of the dominant arm projects from the second end 111c.

Specially, the rotary axis J of the joint 35 about which the rotating plate 251 rotates is located to have the minimum distance L between the rotary axis J and the point end of the elbow E of the dominant arm located on the elbow holder 113; the minimum distance L is set to be equal to or longer than 50 mm or more preferably to be equal to or longer than 70 mm and equal to or shorter than 100 mm. Because, in the exemplary embodiment, the hand portion of the doctor's dominant arm projects from the first end 111b of the mount 111, the rotary axis J is located between the wrist W and the elbow E of the doctor's dominant arm. This configuration of the arm holder 11 results in an improvement of the doctor's operability using the arm support apparatus 1.

Specifically, if the minimum distance L was set to be shorter than 50 mm (see FIG. 5A), there would be a large swing angle of the doctor's fingertips when the doctor D rotates the arm holder 11 about the rotary axis J, resulting in reduction of the doctor's operability using the arm support apparatus 1 during doctor's precise operations, i.e. precise surgery operations.

In contrast, in the arm support apparatus 1, the rotary axis J of the joint 35 is located to be far from the point end of the elbow E of the dominant arm located on the elbow holder 113 by at least 50 mm within the range between the wrist W and the point end of the elbow E of the doctor's dominant arm (see FIG. 5B). This configuration makes it possible to scale down rotation of the elbow E about the rotary axis J, and move the doctor's fingertips based on scaled-down rotation of the elbow E. This therefore results in easy control of movement of the doctor's fingertips during precise operations, i.e. precise surgery operations.

In other words, the rotary axis J of the joint 35 about which the rotating plate 251 rotates is located to enable both the first and second ends 111b and 111c of the mount 111 to swing about the rotary axis J while preventing or limiting the mount 111 from swinging about the first end 111b, i.e. the elbow locator 113. That is, if the minimum distance L was set to be shorter than 50 mm (see FIG. 5A), swing of the mount 111 about the rotary axis J would be substantially equivalent to swing of the mount 111 about the first end 111b1, i.e. the elbow locator 113.

These results when the minimum distance L was set to be shorter than 50 mm (see FIG. 5A), or set to be equal to or longer than 50 mm (preferably set to be equal to or longer than 70 mm and equal to or shorter than 100 mm) were obtained by many experiments based on prototypes of the arm support apparatus 1 in close cooperation with many operators, such as doctors.

This configuration prevents or limits the forearm A mounted on the mount 111 from swinging about the elbow E located on the elbow locator 113. This prevents or limits the doctor's fingertips from largely swinging about the rotary axis J even if the doctor D moves, i.e. swings, the elbow E about the rotary axis J, resulting in maintenance of doctor's operability using the arm support apparatus 1 during doctor's precise operations, i.e. precise surgery operations.

If the rotary axis J of the joint 35 was located to be within the range between the wrist W and the fingertips of the doctor's dominant arm, the arm holder 11 and/or the holder supporter 25 could interfere with an object being operated, such as a patient being operated. However, the arm support apparatus 1 according to the exemplary aspect avoids the occurrence of such interference.

In addition, the arm support apparatus 1 includes a mechanism for adjusting the position of the rotary axis J of the joint 35 with respect to the elbow E, in other words, with respect to the wrist W. The mechanism is composed of the adjustment holes 115, the bolt holes 253, and the bolts 116. That is, inserting the two bolts 116 into selected adjacent two adjustment holes 115 and the bolt holes 253 respectively aligned with the selected adjacent two adjustment holes 115 makes it possible to adjust the position of the rotary axis J in the longitudinal direction of the forearm A according to the doctor's needs.

The arm support apparatus 1 has rotational resistance of the rotating plane 251, i.e. sliding friction between the rotating shaft 35a and the bearing 35b, adjusted to be set within the range from 0.01 to 0.1 Nm inclusive. If the rotational resistance of the rotating plate 251 was lower than the range from 0.01 to 0.1 Nm inclusive, the doctor E could excessively move the forearm A, resulting in reduction of the doctor's operability using the arm support apparatus 1. Otherwise, if the rotational resistance of the rotating plate 251 was greater than the range from 0.01 to 0.1 Nm inclusive, it could be difficult for the doctor E to move the forearm A.

However, as described above, the arm support apparatus 1 has rotational resistance of the rotating plane 251, suitably adjusted to be set within the range from 0.01 to 0.1 Nm inclusive. This configuration makes it possible for the doctor D to easily perform fine movement of the forearm A, resulting in further improvement of the doctor's operability during precise operations, i.e. precise surgery operations.

These results when the rotational resistance of the rotating plate 251 was lower or higher than the range from 0.01 to 0.1 Nm inclusive or within the range from 0.01 to 0.1 Nm inclusive were obtained by many experiments based on prototypes of the arm support apparatus 1 in close cooperation with many operators, such as doctors.

The arm support apparatus 1 is configured such that no brakes are attached to the joint 35 having the rotary axis J around which the arm holder 11 turns. This configuration makes it possible to rotate the arm holder 11 about the rotary axis J while the controller 100 operates in the lock mode.

In other words, the arm support apparatus 1 is configured such that the brakes 31A, 32A, 33A, and 34A are attached to the respective joints 31, 32, 33, and 34 except for the joint 35 for limitation of the respective rotations of the joints 31, 32, 33, and 34. This configuration allows the doctor D to adjust the orientation of the forearm A, i.e. the hand portion, about the rotary axis J while the controller 100 operates in the lock mode in which the joints 31 to 34 are locked. This allows the doctor D to freely rotate the forearm A about the rotary shaft J while the forearm A is mounted on the arm holder 11 in the lock mode. This configuration makes it possible for the doctor D to perform precise and long operations with light fatigue. Particularly, this configuration brings an efficient effect when the doctor D stitches up treated portions of a patient in millimeters.

As described above, the arm support apparatus 1 is configured to adjust the location of the arm holder 11 in the longitudinal direction of the doctor's forearm A. Thus, the doctor D can adjust a rotational-movement range of the forearm A about the rotary axis J according to information of the surgery operations, the doctor's needs, and/or the doctor's physical features. This results in further improvement of the doctor's operability using the arm support apparatus 1.

Particularly, the mechanism for fixing the arm holder 11 using the bolts 116 in the direction perpendicular to the longitudinal direction of the doctor's forearm A is used as the mechanism for adjusting the location of the arm holder 11 in the longitudinal direction of the doctor's forearm A. This stably fixes the mount 111 to the holder support 25 even if the forearm A is moved in the longitudinal direction thereof.

The present disclosure is not limited to the aforementioned exemplary embodiment, and various modifications of the exemplary embodiment can be performed within the scope of the present disclosure.

The rotational resistance of the rotating plate 251 can be adjusted to be set outside the range from 0.01 to 0.1 Nm. The number of joints of the multijoint arm 12 can be changed to another number. The number of counterweights of the multijoint arm 21 can be changed to another number. The shape of the arm holder 11 can be changed to another shape. The arm support apparatus 1 can be applied to various operations except for surgical operations, such as precision-machine manufacturing.

While an illustrative embodiment of the present disclosure has been described herein, the present disclosure is not limited to the embodiments described herein, but includes any and all embodiments having modifications, omissions, combinations (e.g., of aspects across various embodiments), adaptations and/or alternations as would be appreciated by those in the art based on the present disclosure. The limitations in the claims are to be interpreted broadly based on the language employed in the claims and not limited to examples described in the present specification or during the prosecution of the application, which examples are to be construed as non-exclusive.

What is claimed is:

1. An arm support apparatus for supporting an arm of an operator, the arm support apparatus comprising:
    an arm holder having a longitudinal mount on which a forearm of the operator's arm is mountable, the longitudinal mount having a first end and a second end opposite to the first end in a longitudinal direction thereof;
    an elbow locator provided on the first end of the mount, the elbow locator locating an elbow of the operator's arm when the forearm is mounted on the mount;
    a multijoint supporting member having a plurality of joints and movably supporting the mount via motions of the joints; and
    at least one weight provided on at least part of the multijoint supporting member, the at least one weight suppressing movement around at least one of the joints based on gravity while the forearm is mounted on the mount,
    the joints including a rotary joint having a rotary axis, the rotary axis having a vertical component, the mount being rotatably joined to the rotary joint, while the forearm is mounted on the mount so that the elbow of the operator's arm is located by the elbow locator, the rotary axis being located with a distance with respect to the elbow to enable both the first and second ends of the mount to swing about the rotary axis, the distance being set to be equal to or longer than 50 mm, wherein
    the arm holder comprises a rotating member rotatably joined to the rotary joint, the mount being mounted on a surface of the rotating member,
    the mechanism comprises:
    a plurality of adjustment holes formed through the mount and aligned in the longitudinal direction of the mount;
    at least one hole formed on the surface of the rotating member; and
    at least one bolt being fixedly fitted through at least one selected adjustment hole in the plurality of adjustment holes in the at least one hole of the rotating member.

2. An arm support apparatus for supporting an arm of an operator, the arm support apparatus comprising:
    an arm holder having a longitudinal mount on which a forearm of the operator's arm is mountable, the longitudinal mount having a first end and a second end opposite to the first end in a longitudinal direction thereof;
    an elbow locator provided on the first end of the mount, the elbow locator locating an elbow of the operator's arm when the forearm is mounted on the mount;
    a multijoint supporting member having a plurality of joints and movably supporting the mount via motions of the joints; and
    at least one weight provided on at least part of the multijoint supporting member, the at least one weight suppressing movement around at least one of the joints based on gravity while the forearm is mounted on the mount,
    the joints including a rotary joint having a rotary axis, the rotary axis having a vertical component, the mount being rotatably joined to the rotary joint, while the forearm is mounted on the mount so that the elbow of the operator's arm is located by the elbow locator, the rotary axis being located with a distance with respect to the elbow to enable both the first and second ends of the mount to swing about the rotary axis, the distance being set to be equal to or longer than 50 mm, wherein
    the arm holder comprises a rotating member rotatably joined to the rotary joint, the mount being mounted on a surface of the rotating member,
    the mechanism comprises:
    a plurality of adjustment holes formed through the amount and aligned in the longitudinal direction of the mount;
    at least one hole formed on the surface of the rotating member; and
    at least one bolt being fixedly fitted through at least one selected adjustment hole in the plurality of adjustment holes in the at least one hole of the rotating member.

3. The arm support apparatus according to claim 1, wherein the distance is set to be equal to or shorter than 100 mm.

4. The arm support apparatus according to claim 1, wherein rotational resistance of the longitudinal mount via the rotary joint is adjusted to he set within a range from 0.01 to 0.1 Nm inclusive.

5. The arm support apparatus according to claim 1, further comprising:
    a mechanism that fixedly supports the longitudinal mount to the rotary joint while a position of the rotary shaft relative to the first end of the longitudinal mount is adjustable.

6. The arm support apparatus according to claim 1, further comprising:
    a brake attached to at least one of the joints except for the rotary joint and operative to limit motion of the at least one of the joints.

7. The arm support apparatus according to claim 6, wherein the brake comprises a plurality of brakes, the brakes being attached to the respective joints except for the rotary joint and operative to limit motions of the corresponding joints.

8. The arm support apparatus according to claim 5, wherein the longitudinal mount has a substantially concave U shape in a lateral cross section thereof, and has an inner surface on which the forearm of the operator'arm is mountable.

9. The arm support apparatus according to claim 8, further comprising:
    a mechanism that fixedly supports the longitudinal mount to the rotary joint while a position of the rotary shaft relative to the first end of the longitudinal mount is adjustable.

* * * * *